United States Patent
Tran et al.

(10) Patent No.: US 12,410,450 B1
(45) Date of Patent: Sep. 9, 2025

(54) METHOD FOR PRODUCING HYDROGEN GAS FROM SWEET SORGHUM

(71) Applicant: Quyen Dinh Tran, Ho Chi Minh (VN)

(72) Inventors: Quyen Dinh Tran, Ho Chi Minh (VN); Binh Van Nguyen, Ho Chi Minh (VN)

(73) Assignees: Quyen Dinh Tran, Ho Chi Minh (VN); Binh Van Nguyen, Ho Chi Minh (VN)

( * ) Notice: Subject to any disclaimer, the term of this patent is extended or adjusted under 35 U.S.C. 154(b) by 0 days.

(21) Appl. No.: 18/946,900

(22) Filed: Nov. 13, 2024

(30) Foreign Application Priority Data

May 17, 2024 (VN) ............................... 1-2024-03548

(51) Int. Cl.
| | |
|---|---|
| *C12P 3/00* | (2006.01) |
| *C12N 1/20* | (2006.01) |
| *C12N 9/26* | (2006.01) |
| *C12N 9/34* | (2006.01) |
| *C12R 1/01* | (2006.01) |
| *C12R 1/145* | (2006.01) |

(52) U.S. Cl.
CPC ............... *C12P 3/00* (2013.01); *C12N 1/205* (2021.05); *C12N 9/2414* (2013.01); *C12N 9/2428* (2013.01); *C12R 2001/01* (2021.05); *C12R 2001/145* (2021.05); *C12Y 302/01001* (2013.01); *C12Y 302/01003* (2013.01)

(58) Field of Classification Search
CPC ......... C12P 3/00; C12N 1/205; C12N 9/2414; C12N 9/2428; C12R 2001/01; C12R 2001/145; C12Y 302/01001; C12Y 302/01003
See application file for complete search history.

(56) References Cited

U.S. PATENT DOCUMENTS 10,323,260 B2 * 6/2019 Kraemer ................... C12P 7/14

FOREIGN PATENT DOCUMENTS

CN    116590350 A  *  8/2023

OTHER PUBLICATIONS

Dareioti et al., Dark Fermentation of Sweet Sorghum Stalks, Cheese Whey and Cow Manure Mixture: Effect of pH, Pretreatment and Organic Load. Processes. 2021; 9(6):1017. (Year: 2021).*

Morsy, F. M., CO2-free biohydrogen production by mixed dark and photofermentation bacteria from sorghum starch using a modified simple purification and collection system, Energy, vol. 87, 2015, pp. 594-604. (Year: 2015).*

English translation of CN116590350A (Chen et al.) (Year: 2023).*

* cited by examiner

*Primary Examiner* — Robert B Mondesi
*Assistant Examiner* — Naghmeh Nina Moazzami (57) ABSTRACT

A method for producing hydrogen gas ($H_2$) from sweet sorghum (*Sorghum bicolor* (L.) Moench) comprising: (i) preparing materials; (ii) creating a first temporary mixture; (iii) creating a second temporary mixture; (iv) creating a third temporary mixture; (v) creating a first base mixture; (vi) fermenting the first base mixture under dark conditions to produce a first hydrogen gas and a dark fermented base mixture; (vii) creating a second base mixture; (viii) fermenting the second base mixture under light conditions to produce a second hydrogen gas; and (ix) purifying the first hydrogen gas and the second hydrogen gas to obtain a hydrogen gas purity of over 99%.

13 Claims, 1 Drawing Sheet
Specification includes a Sequence Listing.

SEQUENCE LISTING

```
Sequence total quantity: 3
SEQ ID NO: 1            moltype = DNA  length = 1338
FEATURE                 Location/Qualifiers
source                  1..1338
                        mol_type = genomic DNA
                        organism = Clostridium acetobutylicum
SEQUENCE: 1
cagcggcgga cgggtgagta tcacgtgggt aacctacctc atagtgggga atagcctttc   60
gataggaaga ttaataccgc ataatactcg agaatcgcat gattcttgag ccaaaggatt  120
tattcgctat gagatggacc cgcggcgcat tagcttgttg gtgaggtaac ggctcaccaa  180
ggcttcgatg cgtagccgac ctgagagggt gatcggccac attggaactg ggacacggtc  240
cagactccta cgggaggcag cagtggggaa tattgcacaa tgggggaaac cctgatgcag  300
caacgccgcg tgagtgatga aggtcttcgg atcgtaatac tctgtcttat gggacgataa  360
tgacggtacc ataggaggaa gccacggcta actacgtgcc agcagccgcg gtaatacgta  420
ggtggcaagc gttgtccgga tttactgggc gtaaaggatg tgtaggcgga tatttaagtg  480
agatgtgaaa tccccgggct taacttggcg gctgcatttc aaactggatg tctggagtgc  540
aggagaggaa ggcagaattc ctagtgtagc ggtgaaatgc gtagagatta ggaagaatac  600
cagtggcgaa ggcggccttc tggactgtaa ctgacgctga ggcatgaaag cgtggggagc  660
aaacaggatt agataccctg gtagtccacg ccgtaaacga tgaatactag gtgtaggagg  720
tatcgactcc ttctgtgccg cagttaacac aataagtatt ccgcctggga agtacggtcg  780
caagattaaa actcaaagga attgacgggg acccgcacaa gcagcggagc atgtggttta  840
attcgaagca acgcgaagaa ccttacctag acttgacatc tcctgaatta gtccgtaatg  900
gatgaagtcc cttcggggac aggatgacag gtggtgcatg gttgtcgtca gctcgtgtcg  960
tgagatgttg ggttaagtcc cgcaacgagc gcaaccctta tcattagttg ctaacattta 1020
gttgagcact ctagtgagac tgcccgggtt aaccgggagg aaggtgggga tgacgtcaaa 1080
tcatcatgcc ccttatgtct agggctacac acgtgctaca atggtgggga caataagatg 1140
caataccgca agtggagcaa aactcaaaac cccatcccag ttcggattgt aggctgaaac 1200
tcgcctacat gaagccggag ttgctagtaa tcgcgaatca gaatgtcgcg gtgaatacgt 1260
tcccgggtct tgtacacacc gcccgtcaca ccatgagagt cggcaacacc cgaagcccgt 1320
gaggtaacct tttggaac                                               1338

SEQ ID NO: 2            moltype = DNA  length = 1514
FEATURE                 Location/Qualifiers
source                  1..1514
                        mol_type = genomic DNA
                        organism = Caldicellulosiruptor saccharolyticus
SEQUENCE: 2
ctggctcagg acgaacgctg gcggcgtgcc taacgcatgc aagtcgagcg gagatggtgg   60
ttgaaggtga tgagctggag gctgccaact tagcggcgga cgggtgagta acacgtgagc  120
aacctacccc cagcacgggg ataacagctc gaaagggctc ctaataccg atgggaccac  180
gtcatcgcat ggtgatgtgg tatagggta gccgggagg ctatactggc tgggatggg    240
ctcgcggccc atcagctagt tggtgggta acggcctacc aaggcgacga cgggtagccg   300
gcctgagagg gtgtacggcc acagtgggac tgagacacg cccacactcc tacgcgaggc   360
agcagcgggg aatcttcgc aatgggcgga agcctgacgc agcgacgccg cgtgagggag   420
gaagcccttc ggggtgtaaa cctctttgga cggggagaag taggagatag tacccgttta   480
```

```
aaaagccacg gctaactacg tgccagcagc cgcggtaata cgtaggtggc gagcgttgtc  540
cggaattact gggcgtaaag ggtgcgtagg cggctatgcg agttaagcgt gaaagcctta  600
ggctcaacct aaggattgcg cttaatactg catagcttga gtgcgcgaga ggacggcgga  660
attcccggtg tagcggtgaa atgcgtagat atcgggagga acaccagtgg cgaaggcggc  720
cgtctggacc gtaactgacg ctgaggcacg aaagcgtggg gagcgaacag gattagatac  780
cctggtagtc cacgctgtaa acgatggatg ctaggtgtgg gggagaagga ctcctccgtg  840
ccgtagttaa cacaataagc atcccgcctg gggagtacgg ccgcaaggtt gaaactcaaa  900
ggaattgacg ggggcccgca caagcggtgg agcatgtggt ttaattcgaa gcaacgcgaa  960
gaaccttacc agggcttgac atgccggga cctgcccgaa agggtggggt gcctgaccgt  1020
aaggttagga gcccggacac aggtggtgca tggttgtcgt cagctcgtgt cgtgagatgt  1080
tgggttaagt cccgcaacga gcgcaacccc tgcccttagt tgccagcgcg taatggtggg  1140
cactctaagg ggactgccgt cgatgaggcg gaggaaggtg gggatgacgt caaatcatca  1200
tgcccctat gccctgggct acacacgtgc tacaatgggt gctacagagg gcgtgcgaag  1260
gcgcgagccg gagcgaatcc caataaagca cccccagttc ggattgcagg ctgcaactcg  1320
cctgcatgaa gtcggaatcg ctagtaatcg cggatcagca tgccgcggtg aatacgttcc  1380
cgggccttgt acacaccgcc cgtcacacca tgagagtcag caacacctga agacacaggg  1440
cagctgtgtt gaaggtgggg ctgatgattg gcgtgaagtc gtaacaaggt agccgtacgg  1500
gaacgtgcgg ctgg                                                    1514

SEQ ID NO: 3           moltype = DNA  length = 1306
FEATURE                Location/Qualifiers
source                 1..1306
                       mol_type = genomic DNA
                       organism = Rhodobacter sphaeroides
SEQUENCE: 3
gaagtcttcg gacttagcgg cggacgggtg agtaacgcgt gggaacgtgc cctttgcttc  60
ggaatagccg cggggaaactg ggagtaatac cgaatgtgcc ctttggggga aagatttatc  120
ggcaaaggat cggcccgcgt tggattaggt agttggtggg gtaatggcct accaagccga  180
cgatccatag ctggtttgag aggatgatca gccacactgg gactgagact cggcccagac  240
tcctacggga ggcagcagtg gggaatctta gacaatgggc gcaagcctga tctagccatg  300
ccgcgtgatc gatgaaggcc ttagggttgt aaagatcttt caggtgggaa gataatgacg  360
gtaccaccag aagaagcccc ggctaactcc gtgccagcag ccgcggtaat acggaggggg  420
ctagcgttat tcggaattac tgggcgtaaa gcgcacgtag gcggatcgga aagtcagagg  480
tgaaatccca gggctcaacc ctggaactgc ctttgatact cccgatcttg aggtcgagag  540
aggtgagtgg aattccgagt gtagaggtga aattcgtaga tattcggagg aacaccagtg  600
gcgaaggcgg ctcactggct cgatactgac gctgaggtgc gaaagcgtgg ggagcaaaca  660
ggattagata ccctggtagt ccacgccgta aacgatgaat gccagtcgtc gggcagcatg  720
ctgttcggtg acacacctaa cggattaagc attccgcctg gggagtacgg ccgcaaggtt  780
aatactcaaa ggaattgacg gcggcccgca caagcggtgg agcatgtggt ttaattcgaa  840
gcaacgcgca gaaccttacc aacccttgac atggcgatcg cggttccaga gatggttcct  900
tcagttcggc tggatcgcac acaggtgctg catggctgtc gtcagctcgt gtcgtgagat  960
gttcggttaa gtccggcaac gagcgcaacc cacgtcctta gttgccagca ttcagttggg  1020
cactctaggg aaactgccgg tgataagccg gaggaaggtg tggatgacgt caagtcctca  1080
tggcccttac gggttgggct acmcacgtgc tacaatggca gtgacaatgg gttaatccca  1140
ataagctgtc tcagttcgga ttggggtctg caactcgacc ccatgatgtc ggaatcgcta  1200
gtaatcgcgt aacagcatga cgcggtgaat acgttcccgg gccttgtaca caccgcccgt  1260
cacaccatgg gaattggttc tacccgaagg cggtgcgcca acctcg                 1306
```

METHOD FOR PRODUCING HYDROGEN GAS FROM SWEET SORGHUM

CLAIM OF PRIORITY

This application claims priority under 35 U.S.C. § 112 (d) of Application No. 1-2024-03548, filed on 17 May 2024, in the Republic Socialist of Vietnam. The patent application identified above is incorporated here by reference in its entirety.

INCORPORATION BY REFERENCE OF MATERIAL SUBMITTED ELECTRONICALLY

This application contains, as a separate part of disclosure, a sequence listing in computer-readable form (filename: TTH_001_SL.xml; 7,382 bytes; created Nov. 1, 2024) which is incorporated by reference in its entirety.

FIELD OF THE INVENTION

This invention falls within the fields of biotechnology and renewable energy technology. Specifically, the present invention relates to a method for producing hydrogen gas ($H_2$) from the sugar juice extracted from the stalks and the starch of the seeds of sweet sorghum. The invention encompasses the processes of extraction, material treatment, enzyme and microbial fermentation management, and steps for controlling fermentation conditions to optimize hydrogen gas production. The techniques employed in the method aim to maximize the efficiency of converting biomass into hydrogen gas while ensuring sustainability and environmental effectiveness.

BACKGROUND ART

In the field of renewable energy, exploring and developing alternative energy sources to reduce dependence on fossil fuels is a significant research topic. Hydrogen gas ($H_2$) is considered one of the cleanest and most efficient energy sources, with the potential to replace traditional fuels. Hydrogen is a very clean fuel; when burned, it only produces water and does not emit greenhouse gases.

One common method of hydrogen production is water electrolysis. However, this method requires a large amount of electrical energy, which is often generated from non-renewable sources. Therefore, finding sustainable and environmentally friendly methods for hydrogen production has become a priority.

Using biomass is an attractive approach for hydrogen production, as it not only helps recycle abundant raw materials but also has the potential to recover energy from waste. Among biomass materials, sweet sorghum (*Sorghum bicolor* (L.) Moench) stands out due to its rapid growth and high sugar content in the stalks and starch in the seeds, which can be converted into sugars and subsequently into hydrogen through fermentation.

Previous studies have explored the fermentation of biomass to produce hydrogen using various microorganisms. Bacterial strains such as *Clostridium* and *Rhodobacter* have been extensively studied for their hydrogen production capabilities. However, most research has focused on anaerobic fermentation, with less attention given to combining dark fermentation and light fermentation in a single process. This combination has the potential to increase the overall efficiency of hydrogen production by optimizing the growth conditions of the microorganisms.

Despite significant advancements in biomass-based hydrogen production, many challenges remain, such as improving efficiency, reducing costs, and optimizing fermentation conditions. Therefore, providing a new method for producing hydrogen gas from plant-based materials like sweet sorghum, with technical and economic improvements, is necessary and promises substantial benefits for society and the environment.

Furthermore, it is necessary to create a method for producing hydrogen gas ($H_2$) from sweet sorghum (*Sorghum bicolor* (L.) Moench) comprising: (i) preparing materials; (ii) creating a first temporary mixture; (iii) creating a second temporary mixture; (iv) creating a third temporary mixture; (v) creating a first base mixture; (vi) fermenting the first base mixture under dark conditions to produce a first hydrogen gas and a dark fermented base mixture; (vii) creating a second base mixture; (viii) fermenting the second base mixture under light conditions to produce a second hydrogen gas; and (ix) purifying the first hydrogen gas and the second hydrogen gas to obtain a hydrogen gas purity of over 99%.

It is also essential to provide a method for producing hydrogen gas from sweet sorghum using biotechnology, with simple implementation steps that can be applied on an industrial scale, providing the market with safe and quality hydrogen products.

This invention provides solutions to achieve the above goals.

SUMMARY OF THE INVENTION

Accordingly, the first objective of the present invention is to provide a method for producing hydrogen gas ($H_2$) from sweet sorghum (*Sorghum bicolor* (L.) Moench) comprising steps performed in the following specific order:

(i) preparing materials including: a sweet sorghum stalk juice ingredient, a sweet sorghum seed powder ingredient, an alpha-amylase enzyme ingredient, a glucoamylase enzyme ingredient, an organic acid ingredient, a dark fermentation microorganism ingredient, and a light fermentation microorganism ingredient;
  wherein the sweet sorghum stalk juice ingredient is obtained by heating the juice from sweet sorghum stalks at 60° C.-70° C. until the Brix level reaches 15-18° Bx;
  wherein the sweet sorghum seed powder ingredient is finely ground to a size of 1-2 mm and having a moisture content of less than 12%;
  wherein the organic acid ingredient is selected from the group consisting of butyric acid, acetic acid, and combinations thereof;
  wherein the dark fermentation microorganism ingredient is obtained by mixing a first increased density solution with a second increased density solution in a ratio of (1-3):(1-3);
  in which, prepare the first increased density solution by culturing a first microorganism strain on a first growth medium comprising: glucose ($C_6H_{12}O_6$) at 20 g/L, ammonium sulfate (($NH_4)_2SO_4$) at 5 g/L, potassium phosphate dibasic ($K_2HPO_4$) at 1 g/L, magnesium sulfate heptahydrate ($MgSO_4 \cdot 7H_2O$) at 0.5 g/L, manganese sulfate monohydrate ($MnSO_4 \cdot H_2O$) at 0.02 g/L, cobalt chloride hexahydrate at 0.01 g/L, vitamin B12 at 0.0001 g/L, and biotin at 0.000005 g/L;
    wherein the first microorganism strain is selected from a group consisting of *Clostridium acetobutylicum* ATCC 824 (with a designated identifier in the gene bank being AE001438.3), *Clostridium acetobutylicum* ATCC 4259 (with a designated identifier in the gene bank being U09978.1), *Clostridium acetobutylicum* ATCC 39058 (with a designated identifier in the gene bank being U16164.1), and *Clostridium acetobutylicum* TT01 (SEQ ID No. 1);

in which, prepare the second increased density solution by culturing a second microorganism strain on a second growth medium comprising: cellobiose at 5 g/L, peptone at 5 g/L, yeast extract at 5 g/L, sodium bicarbonate ($NaHCO_3$) at 3.5 g/L, ammonium sulfate (($NH_4$)$_2SO_4$) at 3 g/L, resazurin at 0.001 g/L, L-cysteine hydrochloride at 0.1 g/L, vitamin B12 at 0.0001 g/L, and biotin at 0.000005 g/L;

wherein the second microorganism strain is selected from a group consisting of *Caldicellulosiruptor saccharolyticus* Tp8T.6331 (with a designated identifier in the gene bank being NR_036878.1), *Caldicellulosiruptor saccharolyticus* DSM 8903 (with a designated identifier in the gene bank being NR_074845.1), and *Caldicellulosiruptor saccharolyticus* TT02 (SEQ ID No. 2);

wherein the dark fermentation microorganism ingredient contains the first microorganism strain with a cell density of $10^9$ CFU/mL and the second microorganism strain with a cell density of $10^9$ CFU/mL;

wherein the light fermentation microorganism ingredient is obtained by culturing a third microorganism strain on a third growth medium comprising: glucose ($C_6H_{12}O_6$) at 10 g/L, yeast extract at 5 g/L, peptone at 5 g/L, sodium chloride (NaCl) at 5 g/L, magnesium sulfate heptahydrate ($MgSO_4 \cdot 7H_2O$) at 1 g/L, potassium dihydrogen phosphate ($KH_2PO_4$) at 1 g/L, and calcium chloride dihydrate ($CaCl_2 \cdot 2H_2O$) at 0.1 g/L;

wherein the third microorganism strain is selected from a group consisting of *Rhodobacter sphaeroides* KD131 (with a designated identifier in the gene bank being CP001150.1), *Rhodobacter sphaeroides* ATCC 17029 (with a designated identifier in the gene bank being CP000579.1), *Rhodobacter sphaeroides* ND42 (with a designated identifier in the gene bank being pp 702412.1), and *Rhodobacter sphaeroides* TT03 (SEQ ID No. 3);

wherein the light fermentation microorganism ingredient contains the third microorganism strain with a cell density of $10^9$ CFU/mL;

(ii) creating a first temporary mixture by performing steps (a) to (c), comprising:
(a) mixing the sweet sorghum stalk juice ingredient with the sweet sorghum seed powder ingredient in a ratio of 1:(0.06-0.15) (w/w) at 70° C., then stirring well;
(b) increasing the temperature to 90° C., maintaining at 90° C. for 3-5 minutes; and
(c) reducing the temperature to 85° C., maintaining at 85° C. for 60 minutes;

(iii) creating a second temporary mixture by mixing the alpha-amylase enzyme ingredient with the first temporary mixture in a ratio of (0.05-0.2):1000 (w/w), adjusting the pH to 5.5-6.5, then incubating at 90° C.-100° C. for 30-60 minutes;

(iv) creating a third temporary mixture by performing steps (a') to (c'), comprising:
(a') mixing the glucoamylase enzyme ingredient with the second temporary mixture in a ratio of (0.05-0.2):1000 (w/w), adjusting the pH to 4.0-5.0;
(b') incubating at 90° C.-100° C. for 30-60 minutes; and
(c') cooling to a temperature of 25° C.-30° C.;

(v) creating a first base mixture by performing steps (a") to (c"), comprising:
(a") mixing the glucoamylase enzyme ingredient with the third temporary mixture in a ratio of (0.05-0.2):1000 (w/w) and stirring well to obtain a fourth temporary mixture;
(b") mixing the organic acid ingredient with the fourth temporary mixture in a ratio of (2-5):1000 (w/w) and stirring well to obtain a fifth temporary mixture; and
(c") mixing the dark fermentation microorganism ingredient with the fifth temporary mixture in a ratio of (1-2):1000 (w/w) and stirring well to obtain the first base mixture;

(vi) fermenting the first base mixture under dark conditions at a temperature of 25° C.-30° C. for 22-26 hours to produce a first hydrogen gas and a dark fermented base mixture;
wherein the pH is controlled from 6.0-6.5 and the dissolved oxygen concentration is controlled to be less than 1%;

(vii) creating a second base mixture by mixing the light fermentation microorganism ingredient with the dark fermented base mixture in a ratio of (1-2):1000 (w/w) and stirring well; and (viii) fermenting the second base mixture under light conditions at a light intensity of 1500-2000 lux, a temperature of 25° C.-30° C., a stirring speed of 200-300 rpm, and for a duration of 22-26 hours to produce a second hydrogen gas;
wherein the pH is controlled from 6.5-7.0.

The second objective of the present invention is to provide a method for producing hydrogen gas using homogeneous materials, including sugar juice from stalks and starch from sweet sorghum seeds, ensuring high recovery efficiency and good quality while being environmentally friendly.

The third objective of the present invention is to provide a method for producing hydrogen gas that integrates all the steps of gelatinization, liquefaction, and saccharification combined with fermentation into a single equipment system, facilitating the production process, saving equipment investment costs, and minimizing production costs.

Another objective of the present invention is to provide a method for producing hydrogen from sweet sorghum using biotechnology with simple execution steps, capable of being applied on an industrial scale, and providing the market with safe and high-quality hydrogen products.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWING

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skills in the art that the present invention may be practiced without these specific details. In other instances, well-known methods, procedures, components, and circuits have not been described in detail so as not to unnecessarily obscure aspects of the present invention.

The terms mentioned in this invention, such as *Sorghum bicolor* (L.) Moench, *Clostridium acetobutylicum*, *Caldicellulosiruptor saccharolyticus*, *Rhodobacter sphaeroides*, etc., are Latin terms related to the classification of genus and species of organisms in the fields of Microbiology and Biotechnology.

It should be noted that mixing machine/device, fermenter machine/device, grinding/pressing machine/device, hydrogen gas storage machine/device, hydrogen gas purification machine/device, etc., and other similar machines/devices are well-known in the fields of biomass fermentation for hydrogen production. Therefore, detailed descriptions and operating principles of these machines/devices are not provided to avoid obscuring unnecessary aspects of the invention.

In the context of this invention, the term "dark conditions" shall mean an environment where the ambient illumination is maintained at less than 1 lux. This can be achieved by placing the fermentation vessel in a light-tight enclosure or by employing effective light-shielding methods to ensure that the environment is essentially devoid of light.

In the context of this invention, the term "light conditions" shall mean an environment where the ambient illumination is maintained within a range of 1500 to 2000 lux. This may be achieved by using calibrated artificial or natural light sources, ensuring that the light intensity is consistently controlled within the specified range during the process.

The first aspect of the present application relates to microbial strains stored at Tin Thanh Group Joint Stock Company, including *Clostridium acetobutylicum* TT01, *Caldicellulosiruptor saccharolyticus* TT02, and *Rhodobacter sphaeroides* TT03.

In the present invention, the strain *Clostridium acetobutylicum* TT01 was isolated from a sorghum cultivation soil sample in Phu Yen Province, Vietnam. This is a Gram-negative, rod-shaped bacterial strain. Identification of the strain *Clostridium acetobutylicum* TT01 was based on morphological characteristics and the 16S rRNA gene sequence region. The sequencing results of the 16S rRNA gene region are presented in SEQ ID No.1.

The strain *Clostridium acetobutylicum* TT01 is capable of fermenting a mixture of sweet sorghum stalk juice ingredient and sweet sorghum seed powder ingredient to produce hydrogen gas under dark conditions. This capability is evaluated based on the volume of hydrogen gas generated during the fermentation process, through an experiment assessing the fermentation efficiency of the strain *Clostridium acetobutylicum* TT01. Additionally, the experiment compares fermentation efficiency with reference strains, including *Clostridium acetobutylicum* ATCC 824 (with a designated identifier in the gene bank being AE001438.3), *Clostridium acetobutylicum* ATCC 4259 (with a designated identifier in the gene bank being U09978.1), and *Clostridium acetobutylicum* ATCC 39058 (with a designated identifier in the gene bank being U16164.1). The results of the experiment are presented in Table 1.

TABLE 1

Results of the experiment assessing the fermentation capability of the strain *Clostridium acetobutylicum* TT01 on a mixture of sweet sorghum stalk juice ingredient and sweet sorghum seed powder ingredient

| Strains | Hydrogen gas volume (mL/L) |
| --- | --- |
| *Clostridium acetobutylicum* TT01 | 286 |
| *Clostridium acetobutylicum* ATCC 824 | 263 |
| *Clostridium acetobutylicum* ATCC 4259 | 254 |
| *Clostridium acetobutylicum* ATCC 39058 | 271 | in which: fermentation was conducted under dark conditions;

the mixing ratio of the sweet sorghum stalk juice ingredient to the sweet sorghum seed powder ingredient was 1:0.15 (w/w);

initial pH was set at 6.5;

fermentation duration was 24 hours;

fermentation temperature was maintained at 30° C.

The results in Table 1 demonstrate that the strain *Clostridium acetobutylicum* TT01 shows the highest fermentation efficiency in converting a mixture of sweet sorghum stalk juice ingredient and sweet sorghum seed powder ingredient into hydrogen gas, reaching 286 mL/L, compared to the other reference strains. Specifically, the strains *Clostridium acetobutylicum* ATCC 824, ATCC 4259, and ATCC 39058 produced only 263 mL/L, 254 mL/L, and 271 mL/L of hydrogen gas, respectively.

In the present invention, the strain *Caldicellulosiruptor saccharolyticus* TT02 was isolated from cow dung samples collected at a cattle farm in Phu Yen Province, Vietnam. This is a Gram-positive, rod-shaped bacterium. The identification of *Caldicellulosiruptor saccharolyticus* TT02 was based on morphological characteristics and 16S rRNA gene sequence analysis. The sequencing results of the 16S rRNA region are presented in SEQ ID No.2.

The strain *Caldicellulosiruptor saccharolyticus* TT02 has the ability to ferment a mixture of sweet sorghum stalk juice ingredient and sweet sorghum seed powder ingredient to produce hydrogen gas under dark conditions. This capability was evaluated based on the hydrogen gas volume generated during fermentation, as part of an experiment assessing the fermentation efficiency of *Caldicellulosiruptor saccharolyticus* TT02. The experiment also compared fermentation efficiency with reference strains, including *Caldicellulosiruptor saccharolyticus* Tp8T.6331 (with a designated identifier in the gene bank being NR_036878.1) and *Caldicellulosiruptor saccharolyticus* DSM 8903 (with a designated identifier in the gene bank being NR_074845.1). The results of the experiment are presented in Table 2.

TABLE 2

Results of fermentation efficiency of *Caldicellulosiruptor saccharolyticus* TT02 on a mixture of sweet sorghum stalk juice ingredient and sweet sorghum seed powder ingredient

| Strains | Hydrogen gas volume (mL/L) |
|---|---|
| *Caldicellulosiruptor saccharolyticus* TT02 | 348 |
| *Caldicellulosiruptor saccharolyticus* Tp8T.6331 | 302 |
| *Caldicellulosiruptor saccharolyticus* DSM 8903 | 322 | in which: fermentation was conducted under dark conditions;
the mixing ratio of the sweet sorghum stalk juice ingredient to the sweet sorghum seed powder ingredient was 1:0.15 (w/w);
initial pH was set at 6.5;
fermentation duration was 24 hours;
fermentation temperature was maintained at 30° C.

Based on Table 2, the experimental results show that the strain *Caldicellulosiruptor saccharolyticus* TT02 has the highest fermentation efficiency in converting the mixture of sweet sorghum stalk juice ingredient and sweet sorghum seed powder ingredient to hydrogen gas, achieving 348 mL/L, which surpasses the reference strains. Specifically, the strains *Caldicellulosiruptor saccharolyticus* Tp8T.6331 and DSM 8903 produced only 302 mL/L and 322 mL/L of hydrogen gas, respectively.

In the present invention, the strain *Rhodobacter sphaeroides* TT03 was isolated from soil samples taken from sweet sorghum fields in Phu Yen Province, Vietnam. This is a Gram-negative, rod-shaped bacterium. The identification of the strain *Rhodobacter sphaeroides* TT03 was based on its morphological characteristics and 16S rRNA gene sequence. The sequencing results of the 16S rRNA region are presented in SEQ ID No.3.

The strain *Rhodobacter sphaeroides* TT03 has the ability to ferment a mixture of sweet sorghum stalk juice ingredient and sweet sorghum seed powder ingredient to produce hydrogen gas under light conditions. This capability was evaluated based on the volume of hydrogen gas generated during fermentation, as part of an experiment assessing the fermentation efficiency of *Rhodobacter sphaeroides* TT03. Additionally, the experiment compared fermentation efficiency with reference strains, including *Rhodobacter sphaeroides* KD131 (with a designated identifier in the gene bank being CP001150.1), *Rhodobacter sphaeroides* ATCC 17029 (with a designated identifier in the gene bank being CP000579.1), and *Rhodobacter sphaeroides* ND42 (with a designated identifier in the gene bank being pp 702412.1). The results of the experiment are presented in Table 3.

TABLE 3

Results of fermentation efficiency of *Rhodobacter sphaeroides* TT03 on on a mixture of sweet sorghum stalk juice ingredient and sweet sorghum seed powder ingredient

| Strains | Hydrogen gas volume (mL/L) |
|---|---|
| *Rhodobacter sphaeroldes* TT03 | 587 |
| *Rhodobacter sphaeroides* KD131 | 511 |
| *Rhodobacter sphaeroides* ATCC 17029 | 526 |
| *Rhodobacter sphaeroides* ND42 | 543 | in which: fermentation conducted under light conditions at an intensity of 1500 lux;
the mixing ratio of the sweet sorghum stalk juice ingredient to the sweet sorghum seed powder ingredient was 1:0.15 (w/w);
initial pH was set at 6.5;
fermentation duration was 24 hours;
fermentation temperature was maintained at 30° C.

The experimental results in Table 3 show that *Rhodobacter sphaeroides* TT03 has the highest efficiency in fermenting the mixture of sweet sorghum stalk juice ingredient and sweet sorghum seed powder ingredient to produce hydrogen gas, reaching 587 mL/L under light conditions. Compared to the reference strains, including *Rhodobacter sphaeroides* KD131, ATCC 17029, and ND42, which generated 511 mL/L, 526 mL/L, and 543 mL/L of hydrogen gas, respectively, TT03 demonstrates a significantly superior efficiency.

The second aspect of the present application relates to a method for producing hydrogen gas ($H_2$) from sweet sorghum (*Sorghum bicolor* (L.) Moench) 100 ("method 100"). Referencing FIG. 1, method 100 begins with at step 101 preparing materials including: a sweet sorghum stalk juice ingredient, a sweet sorghum seed powder ingredient, an alpha-amylase enzyme ingredient, a glucoamylase enzyme ingredient, an organic acid ingredient, a dark fermentation microorganism ingredient, and a light fermentation microorganism ingredient.

Figure 1:
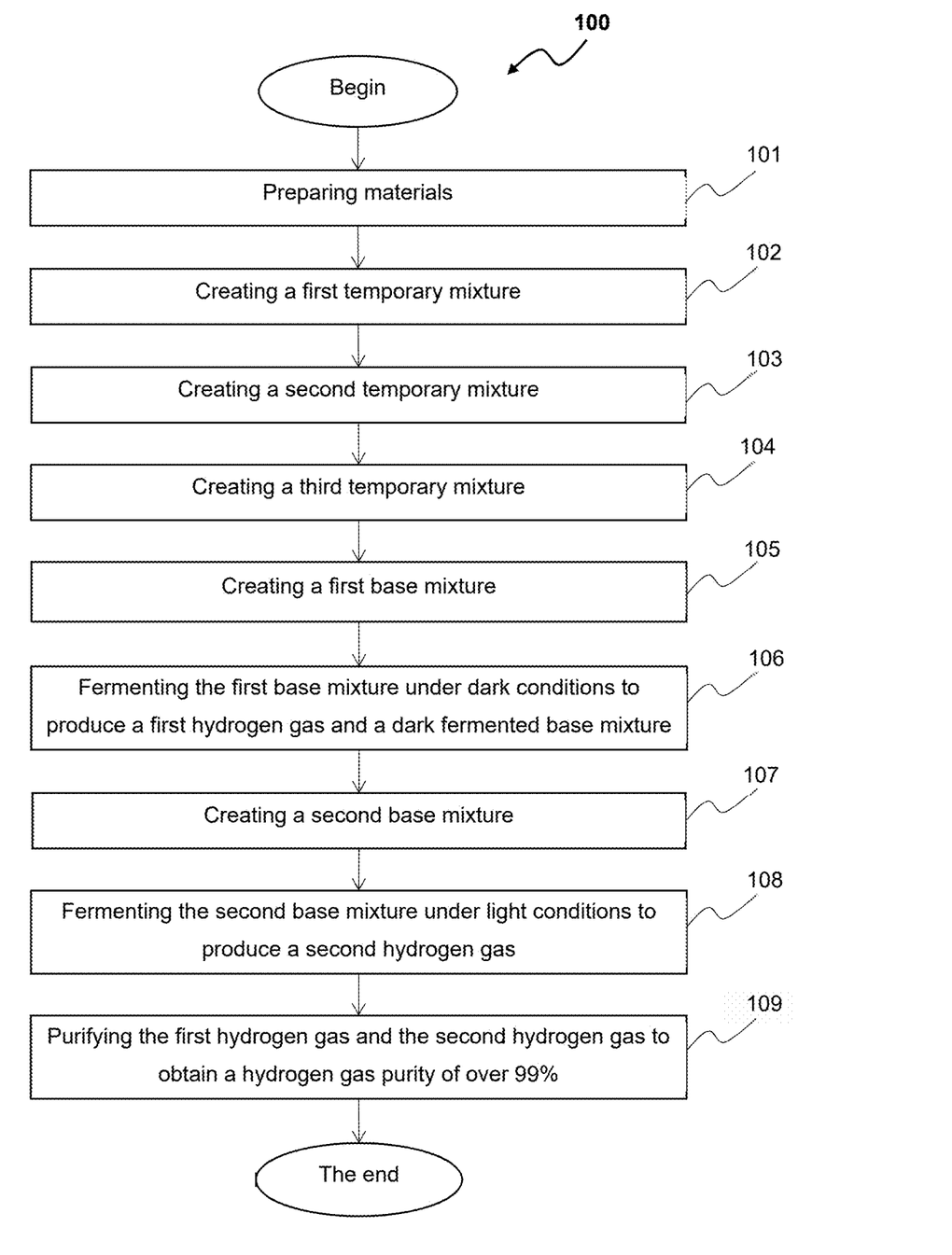
FIG. 1 is a flowchart illustrating a method for producing hydrogen gas ($H_2$) from sweet sorghum 100.

In the present invention, the sweet sorghum stalk juice ingredient is obtained by heating the juice from sweet sorghum stalks at 60° C.-70° C. until the Brix level reaches 15-18° Bx.

In the present invention, the sweet sorghum seed powder ingredient is finely ground to a size of 1-2 mm and having a moisture content of less than 12%.

According to the preferred embodiment of the present invention, the sweet sorghum seed powder ingredient having a starch content of 65% to 70%.

In the present invention, the organic acid ingredient is selected from the group consisting of butyric acid, acetic acid, and combinations thereof.

In the present invention, the dark fermentation microorganism ingredient is obtained by mixing a first increased density solution with a second increased density solution in a ratio of (1-3):(1-3).

In the present invention, the first increased density solution by culturing a first microorganism strain on a first growth medium comprising: glucose ($C_6H_{12}O_6$) at 20 g/L, ammonium sulfate ($(NH_4)_2SO_4$) at 5 g/L, potassium phosphate dibasic ($K_2HPO_4$) at 1 g/L, magnesium sulfate heptahydrate ($MgSO_4 \cdot 7H_2O$) at 0.5 g/L, manganese sulfate monohydrate ($MnSO_4 \cdot H_2O$) at 0.02 g/L, cobalt chloride hexahydrate at 0.01 g/L, vitamin B12 at 0.0001 g/L, and biotin at 0.000005 g/L. Wherein the first microorganism strain is selected from a group consisting of *Clostridium acetobutylicum* ATCC 824 (with a designated identifier in the gene bank being AE001438.3), *Clostridium acetobutylicum* ATCC 4259 (with a designated identifier in the gene bank being U09978.1), *Clostridium acetobutylicum* ATCC 39058 (with a designated identifier in the gene bank being U16164.1), and *Clostridium acetobutylicum* TT01 (SEQ ID No. 1). The preparation of the first growth medium (CGM) is as follows: weigh the components of the medium according to the specified concentrations; dissolve glucose, ammonium sulfate, potassium phosphate dibasic, magnesium sulfate heptahydrate, manganese sulfate monohydrate, and cobalt chloride hexahydrate in distilled water; sterilize the solution at 121° C. for 15 minutes; cool the solution to room temperature (28° C.-32° C.); add vitamin B12 and biotin to the cooled solution; adjust the pH of the solution to 6.8 using hydrochloric acid or sodium hydroxide; filter the solution through sterile filter paper; and distribute the solution into sterile culture flasks.

In the present invention, the second increased density solution by culturing a second microorganism strain on a second growth medium comprising: cellobiose at 5 g/L, peptone at 5 g/L, yeast extract at 5 g/L, sodium bicarbonate ($NaHCO_3$) at 3.5 g/L, ammonium sulfate (($NH_4)_2SO_4$) at 3 g/L, resazurin at 0.001 g/L, L-cysteine hydrochloride at 0.1 g/L, vitamin B12 at 0.0001 g/L, and biotin at 0.000005 g/L. Wherein the second microorganism strain is selected from a group consisting of *Caldicellulosiruptor saccharolyticus* Tp8T.6331 (with a designated identifier in the gene bank being NR_036878.1), *Caldicellulosiruptor saccharolyticus* DSM 8903 (with a designated identifier in the gene bank being NR_074845.1), and *Caldicellulosiruptor saccharolyticus* TT02 (SEQ ID No. 2). The preparation of the second growth medium (DSMZ 12104) is as follows: weigh the components of the medium according to the specified concentrations; dissolve cellobiose, peptone, yeast extract, sodium bicarbonate, and ammonium sulfate in distilled water; sterilize the solution at 121° C. for 15 minutes; cool the solution to room temperature (28° C.-32° C.); add resazurin, L-cysteine hydrochloride, vitamin B12, and biotin to the cooled solution; adjust the pH of the solution to 7.0 using hydrochloric acid or sodium hydroxide; filter the solution through sterile filter paper; and distribute the solution into sterile culture flasks.

In the present invention, the dark fermentation microorganism ingredient contains the first microorganism strain with a cell density of $10^9$ CFU/mL and the second microorganism strain with a cell density of $10^9$ CFU/mL.

According to the preferred embodiment of the present invention, the dark fermentation microorganism ingredient contains the strain *Clostridium acetobutylicum* TT01 (SEQ ID No. 1) at a cell density of $10^9$ CFU/mL and the strain *Caldicellulosiruptor saccharolyticus* TT02 (SEQ ID No. 2) at a cell density of $10^9$ CFU/mL.

According to the preferred embodiment of the present invention, the dark fermentation microorganism ingredient having a mixing ratio of the first increased density solution and the second increased density solution is 1:1.

The mixing of the first increased density solution (the first solution) with the second increased density solution (the second solution) helps to enhance the efficiency of hydrogen fermentation. This has been demonstrated through experiments assessing the hydrogen fermentation efficiency of the dark fermentation microorganism ingredient. The results of the experiment are presented in Table 4.

TABLE 4

Results of the experiment assessing the hydrogen fermentation efficiency of the dark fermentation microorganism ingredient

| Ratio of the first increased density solution:the second increased density solution | $H_2$ yield ($cm^3/s$) | Lactate yield ($cm^3/s$) | Acetate yield ($cm^3/s$) | Ethanol yield ($cm^3/s$) |
|---|---|---|---|---|
| 1:0 | 1.46 | 0.26 | 0.26 | 1.38 |
| 0:1 | 0.76 | 0.64 | 0.45 | 1.56 |
| 3:1 | 1.67 | 0.08 | 0.08 | 1.78 |
| 1:3 | 1.28 | 0.32 | 0.32 | 2.38 |
| 1:1 | 1.9 | 0.06 | 0.06 | 1.63 | in which: values are averages of 3 replicates.

Based on Table 4, the results demonstrate a significant difference in hydrogen production efficiency when adjusting the ratio between the first solution and the second solution. Specifically, when only using the first solution (ratio 1:0), the hydrogen yield reached 1.46 $cm^3/s$, indicating the hydrogen-generating capability of this solution. In contrast, using only the second solution (ratio 0:1) resulted in a yield of 0.76 $cm^3/s$, which is significantly lower, showing that this solution is less effective in hydrogen production compared to the first solution. Notably, when combining the two solutions at different ratios, the hydrogen yield varied significantly. The ratio of 3:1 (more of the first solution) showed a significant increase in yield, reaching 1.67 $cm^3/s$. This suggests that the addition of the second solution enhances the hydrogen-generating capability of the first solution. Conversely, the ratio of 1:3 (more of the second solution) resulted in a decrease in yield to 1.28 $cm^3/s$, but still higher than using the second solution alone. Most remarkably, when the two solutions were mixed at a ratio of 1:1, the hydrogen yield reached its highest level at 1.9 $cm^3/s$. This indicates that an equal mixture of both solutions optimally enhances hydrogen production efficiency.

In the present invention, the light fermentation microorganism ingredient is obtained by culturing a third microorganism strain on a third growth medium comprising: glucose ($C_6H_{12}O_6$) at 10 g/L, yeast extract at 5 g/L, peptone at 5 g/L, sodium chloride (NaCl) at 5 g/L, magnesium sulfate heptahydrate ($MgSO_4 \cdot 7H_2O$) at 1 g/L, potassium dihydrogen phosphate ($KH_2PO_4$) at 1 g/L, and calcium chloride dihydrate ($CaCl_2 \cdot 2H_2O$) at 0.1 g/L. Wherein the third microorganism strain is selected from a group consisting of *Rhodobacter sphaeroides* KD131 (with a designated identifier in the gene bank being CP001150.1), *Rhodobacter sphaeroides* ATCC 17029 (with a designated identifier in the gene bank being CP000579.1), *Rhodobacter sphaeroides* ND42 (with a designated identifier in the gene bank being pp 702412.1), and *Rhodobacter sphaeroides* TT03 (SEQ ID No. 3). Preparation of the third growth medium (YEM-Yeast Extract Medium) is as follows: weigh each component of the medium according to the specified concentrations: glucose, yeast extract, peptone, sodium chloride, magnesium sulfate heptahydrate, monopotassium phosphate, calcium chloride dihydrate, and dissolve them in distilled water; sterilize the solution at 121° C. for 15 minutes; cool to room temperature (28° C.-32° C.); adjust the pH to 7.0 using hydrochloric acid or sodium hydroxide; filter the solution through sterile filter paper; and distribute it into sterile culture flasks.

In the present invention, the light fermentation microorganism ingredient contains the third microorganism strain with a cell density of $10^9$ CFU/mL.

According to the preferred embodiment of the present invention, the light fermentation microorganism ingredient contains the strain *Rhodobacter sphaeroides* TT03 (SEQ ID No. 3) at a cell density of $10^9$ CFU/mL.

At step 102, creating a first temporary mixture by performing steps (a) to (c), comprising:
   (a) mixing the sweet sorghum stalk juice ingredient with the sweet sorghum seed powder ingredient in a ratio of 1:(0.06-0.15) (w/w) at 70° C., then stirring well;
   (b) increasing the temperature to 90° C., maintaining at 90° C. for 3-5 minutes; and
   (c) reducing the temperature to 85° C., maintaining at 85° C. for 60 minutes.

According to the preferred embodiment of the present invention, the ratio of the sweet sorghum stalk juice ingredient and the sweet sorghum seed powder ingredient is 1:0.15 (w/w).

Mixing the sweet sorghum stalk juice ingredient (the stalk juice) with the sweet sorghum seed powder ingredient (the seed powder) enhances the efficiency of hydrogen fermentation. This is demonstrated through an experiment assessing the hydrogen fermentation efficiency of the stalk juice and the sweet powder. The results of the experiment are presented in Table 5.

TABLE 5

Results of the experiment assessing the hydrogen fermentation efficiency of the stalk juice and the seed powder

| Ratio of the stalk juice:the seed powder | Sugar content of juice (%) | Starch content of seeds (%) | Theoretical hydrogen yield (%) | Actual hydrogen yield (%) | Hydrogen fermentation efficiency (%) |
|---|---|---|---|---|---|
| 1:0 | 18.89 | 0 | 1.93 | 1.80 | 93.15$^c$ |
| 1:0.06 | 18.89 | 71.57 | 2.248 | 2.10 | 93.41$^c$ |
| 1:0.09 | 18.89 | 71.57 | 2.407 | 2.25 | 93.55$^b$ |
| 1:0.12 | 18.89 | 71.57 | 2.566 | 2.41 | 93.91$^b$ |
| 1:0.15 | 18.89 | 71.57 | 2.725 | 2.60 | 95.48$^a$ |
| 0:1 | 0 | 71.57 | 1.59 | 1.44 | 90.75$^d$ | in which:
values are averages of 3 replicates;
values within the same column sharing the same letter indicate no statistically significant difference at the 5% level.

in which: values are averages of 3 replicates;
values within the same column sharing the same letter indicate no statistically significant difference at the 5% level.

Based on Table 5, the results show a significant impact of the ratio between the stalk juice and the seed powder on fermentation efficiency. Firstly, when only the stalk juice is used (ratio 1:0), the fermentation efficiency reaches 93.15%, indicating good hydrogen fermentation efficiency. However, when the stalk juice is combined with the seed powder, from a ratio of 1:0.06 to 1:0.15, the fermentation efficiency gradually increases from 93.41% to 95.48%. This indicates that the combination of stalk juice and seed powder enhances the hydrogen fermentation efficiency. Conversely, when only the seed powder is used (ratio 0:1), the fermentation efficiency drops to 90.75%, which is lower than the other ratios. This shows that using the seed powder alone results in lower hydrogen fermentation efficiency compared to combining it with the stalk juice.

At step 103, creating a second temporary mixture by mixing the alpha-amylase enzyme ingredient with the first temporary mixture in a ratio of (0.05-0.2):1000 (w/w), adjusting the pH to 5.5-6.5, then incubating at 90° C.-100° C. for 30-60 minutes.

According to the preferred embodiment of the present invention, the mixing ratio of the alpha-amylase enzyme ingredient and the first temporary mixture is 0.1:1000 (w/w).

At step 104, creating a third temporary mixture by performing steps (a') to (c'), comprising:
(a') mixing the glucoamylase enzyme ingredient with the second temporary mixture in a ratio of (0.05-0.2):1000 (w/w), adjusting the pH to 4.0-5.0;
(b') incubating at 90° C.-100° C. for 30-60 minutes; and
(c') cooling to a temperature of 25° C.-30° C.

According to the preferred embodiment of the present invention, the mixing ratio of the glucoamylase enzyme ingredient and the second temporary mixture is 0.1:1000 (w/w).

At step 105, creating a first base mixture by performing steps (a") to (c"), comprising:
(a") mixing the glucoamylase enzyme ingredient with the third temporary mixture in a ratio of (0.05-0.2):1000 (w/w) and stirring well to obtain a fourth temporary mixture;
(b") mixing the organic acid ingredient with the fourth temporary mixture in a ratio of (2-5):1000 (w/w) and stirring well to obtain a fifth temporary mixture; and
(c") mixing the dark fermentation microorganism ingredient with the fifth temporary mixture in a ratio of (1-2):1000 (w/w) and stirring well to obtain the first base mixture.

According to the preferred embodiment of the present invention, the mixing ratio of the glucoamylase enzyme ingredient and the third temporary mixture is 0.1:1000 (w/w).

According to the preferred embodiment of the present invention, the mixing ratio of the dark fermentation microorganism ingredient and the fifth temporary mixture is 1.5:1000 (w/w).

At step 106, fermenting the first base mixture under dark conditions at a temperature of 25° C.-30° C. for 22-26 hours to produce a first hydrogen gas and a dark fermented base mixture. Wherein the pH is controlled from 6.0-6.5 and the dissolved oxygen concentration is controlled to be less than 1%.

According to the preferred embodiment of the present invention, the fermentation time for the first base mixture under dark conditions is 26 hours.

At step 107, creating a second base mixture by mixing the light fermentation microorganism ingredient with the dark fermented base mixture in a ratio of (1-2):1000 (w/w) and stirring well.

According to the preferred embodiment of the present invention, the ratio of the light fermentation microorganism ingredient and the dark fermented base mixture is 1.5:1000 (w/w).

At step 108, fermenting the second base mixture under light conditions at a light intensity of 1500-2000 lux, a temperature of 25° C.-30° C., a stirring speed of 200-300 rpm, and for a duration of 22-26 hours to produce a second hydrogen gas. Wherein the pH is controlled from 6.5-7.0.

In the present invention, a hydrogen gas obtained from method 100 is a mixture of the first hydrogen gas obtained from fermentation under dark conditions (step 106) and the second hydrogen gas obtained from fermentation under light conditions (step 108).

According to the preferred embodiment of the present invention, the light intensity during the fermentation of the second base mixture is 1500 lux.

According to the preferred embodiment of the present invention, the fermentation time for the second base mixture under light conditions is 24 hours.

Reference Table 6 shows the results of an experiment investigating the hydrogen production efficiency of method 100, applied to produce hydrogen from 440 g of the sweet sorghum stalk juice ingredient 66 g of the sweet sorghum seed powder ingredient, when combining dark fermentation and light fermentation. This experiment compares the hydrogen fermentation efficiency of method 100 with method 100 without light fermentation and method 100 without dark fermentation.

TABLE 6

Results of the experiment investigating the hydrogen production efficiency of method 100

| Experimental condition | Experimental conditions | Hydrogen gas yield (g) |
|---|---|---|
| 1 | Dark fermentation (Method 100 without light fermentation) | 6.56 |
| 2 | Light fermentation (Method 100 without dark fermentation) | 11.84 |
| 3 | Combined dark and light fermentation (Method 100) | 20.64 | in which: values are averages of 3 replicates.

The experimental results on the influence of fermentation conditions on hydrogen gas yield demonstrate significant differences among the methods. In Experiment 1, employing only dark fermentation (without light), the hydrogen gas yield was 6.56 g, indicating that this process can produce hydrogen but with lower efficiency. In contrast, Experiment 2, utilizing only light fermentation (without dark), showed an increased hydrogen yield of 11.84 g, highlighting that fermentation under 1500 lux light significantly enhances hydrogen production efficiency. Particularly noteworthy, Experiment 3, combining both dark and light fermentation conditions, yielded the highest result of 20.64 g of hydrogen gas. This output surpasses the combined yields from the individual methods, underscoring the synergistic effect of employing both dark and light fermentation conditions.

According to the preferred embodiment of the present invention, method 100 further comprises step 109, which involves purifying the first hydrogen gas obtained from the fermentation under dark conditions (step 106) and the second hydrogen gas obtained from the fermentation under light conditions (step 108) to obtain a hydrogen gas purity of over 99%.

In the present invention, method 100 is applied to produce hydrogen gas ($H_2$), including the following steps:
(I) preparing materials:
  prepare 440 g of the sweet sorghum stalk juice ingredient;
  prepare 66 g of the sweet sorghum seed powder ingredient with a moisture content of 9.8% and a starch content of 64.5%;
  prepare 0.05 g of the alpha-amylase enzyme ingredient;
  prepare 0.102 g of the glucoamylase enzyme ingredient;
  prepare 1.518 g of the organic acid ingredient; in which butyric acid is 0.759 g and acetic acid is 0.759 g;
  prepare 0.762 g of the dark fermentation microorganism ingredient; in which the first increased density solution contains 0.381 g of *Clostridium acetobutylicum* TT01 and the second increased density solution contains 0.381 g of *Caldicellulosiruptor saccharolyticus* TT02;
    the dark fermentation microorganism ingredient contains *Clostridium acetobutylicum* TT01 with a cell density of $10^9$ CFU/mL and *Caldicellulosiruptor saccharolyticus* TT02 with a cell density of $10^9$ CFU/mL;
  prepare 0.699 g of the light fermentation microorganism ingredient;
    the light fermentation microorganism ingredient contains *Rhodobacter sphaeroides* TT03 with a cell density of $10^9$ CFU/mL;
(II) creating the first temporary mixture by performing steps (a) to (c):
  (a) mixing 440 g of the sweet sorghum stalk juice ingredient with 66 g of the sweet sorghum seed powder ingredient at 70° C., and stirring well;
  (b) increasing the temperature to 90° C., maintaining at 90° C. for 4 minutes; and
  (c) reducing the temperature to 85° C., maintaining at 85° C. for 60 minutes;
(III) creating the second temporary mixture by mixing 0.05 g of the alpha-amylase enzyme ingredient with 506 g of the first temporary mixture and adjusting the pH to 6.0, then incubating at 100° C. for 60 minutes;
(IV) creating the third temporary mixture by performing steps (a') to (c'):
  (a') mixing 0.051 g of the glucoamylase enzyme ingredient with 506.05 g of the second temporary mixture and adjusting the pH to 4.5;
  (b') incubating at 100° C. for 60 minutes; and
  (c') cooling to a temperature of 28° C.;
(V) creating the first base mixture by performing steps (a") to (c"):
  (a") mixing 0.051 g of the glucoamylase enzyme ingredient with 506.101 g of the third temporary mixture and stirring well to obtain 506.152 g of the fourth temporary mixture;
  (b") mixing 1.518 g of the organic acid ingredient with 506.152 g of the fourth temporary mixture and stirring well to obtain 507.67 g of the fifth temporary mixture; and
  (c") mixing 0.762 g of the dark fermentation microorganism ingredient with 507.67 g of the fifth temporary mixture and stirring well to obtain 508.432 g of the first base mixture;
(VI) fermenting the first base mixture under dark conditions at a temperature of 28° C. for 26 hours to obtain 6.56 g of the first hydrogen gas into the hydrogen gas container and 465.792 g of the dark fermented base mixture; in which the pH is controlled from 6.0 to 6.5 and the dissolved oxygen concentration is controlled to be less than 1%;
(VII) creating the second base mixture by mixing 0.699 g of light fermentation microorganism ingredient with 465.792 g of the dark fermented base mixture and stirring well;
(VIII) fermenting the second base mixture under light conditions at a light intensity of 1500 lux, a temperature of 28° C., a stirring speed of 250 rpm, and a duration of 24 hours to obtain the second hydrogen gas; in which the pH is controlled from 6.5 to 7.0; and
(IX) purifying 20.64 g of the first hydrogen gas obtained from the fermentation under dark conditions (step VI) and the second hydrogen gas obtained from the fermentation under light conditions (step VIII) to obtain hydrogen gas with a purity of over 99%.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method for producing hydrogen gas (H$_2$) from sweet sorghum (*Sorghum bicolor* (L.) Moench) comprising steps performed in the following specific order:
   (i) preparing materials including: a sweet sorghum stalk juice ingredient, a sweet sorghum seed powder ingredient, an alpha-amylase enzyme ingredient, a glucoamylase enzyme ingredient, an organic acid ingredient, a dark fermentation microorganism ingredient, and a light fermentation microorganism ingredient;
   wherein the sweet sorghum stalk juice ingredient is obtained by heating the juice from sweet sorghum stalks at 60° C.-70° C. until the Brix level reaches 15-18° Bx;
   wherein the sweet sorghum seed powder ingredient is finely ground to a size of 1-2 mm and having a moisture content of less than 12%;
   wherein the organic acid ingredient is selected from the group consisting of butyric acid, acetic acid, and combinations thereof;
   wherein the dark fermentation microorganism ingredient is obtained by mixing a first increased density solution with a second increased density solution in a ratio of (1-3):(1-3);
   wherein the first increased density solution is prepared by culturing a first microorganism strain on a first growth medium comprising: glucose (C$_6$H$_{12}$O$_6$) at 20 g/L, ammonium sulfate ((NH$_4$)$_2$SO$_4$) at 5 g/L, potassium phosphate dibasic (K$_2$HPO$_4$) at 1 g/L, magnesium sulfate heptahydrate (MgSO$_4$·7H$_2$O) at 0.5 g/L, manganese sulfate monohydrate (MnSO$_4$·H$_2$O) at 0.02 g/L, cobalt chloride hexahydrate at 0.01 g/L, vitamin B12 at 0.0001 g/L, and biotin at 0.000005 g/L;
   wherein the first microorganism strain is selected from a group consisting of *Clostridium acetobutylicum* (ATCC 824) (with a designated identifier in the gene bank being AE001438.3), and *Clostridium acetobutylicum* (ATCC 4259) (with a designated identifier in the gene bank being U09978.1);
   wherein the second increased density solution is prepared by culturing a second microorganism strain on a second growth medium comprising: cellobiose at 5 g/L, peptone at 5 g/L, yeast extract at 5 g/L, sodium bicarbonate (NaHCO$_3$) at 3.5 g/L, ammonium sulfate ((NH$_4$)$_2$SO$_4$) at 3 g/L, resazurin at 0.001 g/L, L-cysteine hydrochloride at 0.1 g/L, vitamin B12 at 0.0001 g/L, and biotin at 0.000005 g/L;

wherein the second microorganism strain is *Caldicellulosiruptor saccharolyticus* Tp8T.6331 (ATCC 43494) (with a designated identifier in the gene bank being NR_036878.1);

wherein the dark fermentation microorganism ingredient contains the first microorganism strain with a cell density of $10^9$ CFU/mL and the second microorganism strain with a cell density of $10^9$ CFU/mL;

wherein the light fermentation microorganism ingredient is obtained by culturing a third microorganism strain on a third growth medium comprising: glucose ($C_6H_{12}O_6$) at 10 g/L, yeast extract at 5 g/L, peptone at 5 g/L, sodium chloride (NaCl) at 5 g/L, magnesium sulfate heptahydrate ($MgSO_4 \cdot 7H_2O$) at 1 g/L, potassium dihydrogen phosphate ($KH_2PO_4$) at 1 g/L, and calcium chloride dihydrate ($CaCl_2 \cdot 2H_2O$) at 0.1 g/L;

wherein the third microorganism strain is selected from a group consisting of *Rhodobacter sphaeroides* KD131 (KCTC 12085) (with a designated identifier in the gene bank being CP001150.1), and *Rhodobacter sphaeroides* (ATCC 17029) (with a designated identifier in the gene bank being CP000579.1);

wherein the light fermentation microorganism ingredient contains the third microorganism strain with a cell density of $10^9$ CFU/ml;

(ii) creating a first temporary mixture by performing steps (a) to (c), comprising:
(a) mixing the sweet sorghum stalk juice ingredient with the sweet sorghum seed powder ingredient in a ratio of 1:(0.06-0.15) (w/w) at 70° C., then stirring well;
(b) following the mixing and stirring step in (a), increasing the temperature to 90° C., maintaining at 90° C. for 3-5 minutes; and
(c) reducing the temperature to 85° C., maintaining at 85° C. for 60 minutes;

(iii) creating a second temporary mixture by mixing the alpha-amylase enzyme ingredient with the first temporary mixture in a ratio of (0.05-0.2):1000 (w/w), adjusting the pH to 5.5-6.5, then incubating at 90° C.-100° C. for 30-60 minutes;

(iv) creating a third temporary mixture by performing steps (a') to (c'), comprising:
(a') mixing the glucoamylase enzyme ingredient with the second temporary mixture in a ratio of (0.05-0.2):1000 (w/w), adjusting the pH to 4.0-5.0;
(b') incubating at 90° C.-100° C. for 30-60 minutes; and
(c') cooling to a temperature of 25° C.-30° C.;

(v) creating a first base mixture by performing steps (a") to (c"), comprising:
(a") adding the additional glucoamylase enzyme ingredient to the third temporary mixture in a ratio of (0.05-0.2):1000 (w/w) and stirring well to obtain a fourth temporary mixture;
(b") mixing the organic acid ingredient with the fourth temporary mixture in a ratio of (2-5):1000 (w/w) and stirring well to obtain a fifth temporary mixture; and
(c") mixing the dark fermentation microorganism ingredient with the fifth temporary mixture in a ratio of (1-2):1000 (w/w) and stirring well to obtain the first base mixture;

(vi) fermenting the first base mixture under dark conditions at a temperature of 25° C.-30° C. for 22-26 hours to produce a first hydrogen gas and a dark fermented base mixture;
wherein the pH is controlled at 6.0-6.5 and the dissolved oxygen concentration is controlled to be less than 1%;

(vii) creating a second base mixture by mixing the light fermentation microorganism ingredient with the dark fermented base mixture in a ratio of (1-2):1000 (w/w) and stirring well; and (viii) fermenting the second base mixture under light conditions at a light intensity of 1500-2000 lux, a temperature of 25° C.-30° C., a stirring speed of 200-300 rpm, and for a duration of 22-26 hours to produce a second hydrogen gas;
wherein the pH is controlled at 6.5-7.0.

2. The method of claim 1, wherein at step (i) the sweet sorghum seed powder ingredient has a starch content of 65% to 70%.

3. The method of claim 1, wherein at step (i) the dark fermentation microorganism ingredient is obtained by mixing the first increased density solution with the second increased density solution, at a ratio of 1:1.

4. The method of claim 1, wherein at step (ii) the mixing ratio of the sweet sorghum stalk juice ingredient with the sweet sorghum seed powder ingredient is 1:0.15 (w/w).

5. The method of claim 1, wherein at step (iii) the mixing ratio of the alpha-amylase enzyme ingredient with the first temporary mixture is 0.1:1000 (w/w).

6. The method of claim 1, wherein at step (iv) the mixing ratio of the glucoamylase enzyme ingredient with the second temporary mixture is 0.1:1000 (w/w).

7. The method of claim 1, wherein at step (v) the mixing ratio of the glucoamylase enzyme ingredient with the third temporary mixture is 0.1:1000 (w/w).

8. The method of claim 1, wherein at step (v) the mixing ratio of the dark fermentation microorganism ingredient with the fifth temporary mixture is 1.5:1000 (w/w).

9. The method of claim 1, wherein at step (vi) the fermentation time for the first base mixture under dark conditions is 26 hours.

10. The method of claim 1, wherein at step (vii) the mixing ratio of the light fermentation microorganism ingredient with the dark fermented base mixture is 1.5:1000 (w/w).

11. The method of claim 1, wherein at step (viii) the light intensity during the fermentation of the second base mixture is 1500 lux.

12. The method of claim 1, wherein at step (viii) the fermentation time for the second base mixture under light conditions is 24 hours.

13. The method of claim 1, further comprising a step of purifying the first hydrogen gas obtained from the fermentation under dark conditions (step vi) and the second hydrogen gas obtained from the fermentation under light conditions (step viii) to obtain a hydrogen gas purity of over 99%.

* * * * *